(12) United States Patent
Weiss (10) Patent No.: US 12,383,371 B2
(45) Date of Patent: Aug. 12, 2025

(54) SYSTEMS, DEVICES, AND METHODS FOR ROBOTIC PLACEMENT OF ELECTRODES FOR ANATOMY IMAGING

(71) Applicant: Mazor Robotics Ltd., Caesarea (IL)

(72) Inventor: Noam Weiss, Haifa (IL)

(73) Assignee: Mazor Robotics Ltd., Caesarea (IL)

( * ) Notice: Subject to any disclaimer, the term of this patent is extended or adjusted under 35 U.S.C. 154(b) by 52 days.

(21) Appl. No.: 17/498,416

(22) Filed: Oct. 11, 2021

(65) Prior Publication Data

US 2023/0111217 A1    Apr. 13, 2023

(51) Int. Cl.
*A61B 90/00*    (2016.01)
*A61B 34/20*    (2016.01)
*A61B 34/30*    (2016.01)

(52) U.S. Cl.
CPC .............. *A61B 90/39* (2016.02); *A61B 34/20* (2016.02); *A61B 34/30* (2016.02); *A61B 90/37* (2016.02); *A61B 2034/2065* (2016.02); *A61B 2090/373* (2016.02); *A61B 2090/3945* (2016.02)

(58) Field of Classification Search
None
See application file for complete search history.

(56) References Cited

U.S. PATENT DOCUMENTS

| | | | |
|---|---|---|---|
| 8,545,492 B2 | 10/2013 | Mulier et al. | |
| 2013/0012937 A1* | 1/2013 | Mulier | A61B 18/1477 606/33 |
| 2014/0371833 A1* | 12/2014 | Ghosh | A61B 5/316 607/129 |
| 2018/0296277 A1 | 10/2018 | Schwartz et al. | |
| 2019/0015012 A1 | 1/2019 | Raudins et al. | |
| 2019/0274580 A1* | 9/2019 | Krammer | A61B 5/064 |
| 2020/0170723 A1 | 6/2020 | Crawford et al. | |
| 2020/0206521 A1* | 7/2020 | Chen | A61B 3/14 |
| 2021/0128248 A1* | 5/2021 | Cohen | A61B 18/14 |
| 2021/0166812 A1 | 6/2021 | Amir et al. | |

FOREIGN PATENT DOCUMENTS

| | | | |
|---|---|---|---|
| EP | 3035846 | 11/2019 | |
| WO | WO 01/89379 | 11/2001 | |
| WO | WO-2008118727 A1 * | 10/2008 | ........... A61B 5/0035 |
| WO | WO 2017/223120 | 12/2017 | |
| WO | WO-2022013527 A1 * | 1/2022 | ........... A61B 5/0536 |

OTHER PUBLICATIONS

Cheng et al. "A novel robot-assisted electrical impedance scanning system for subsurface object detection," Measurement Science and Technology, 2021, vol. 32, No. 8, 10 pages.

(Continued)

*Primary Examiner* — Christopher Koharski
*Assistant Examiner* — Renee C Langhals
(74) *Attorney, Agent, or Firm* — Sheridan Ross P.C.

(57) ABSTRACT

A method comprises registering a robotic system with a patient based on first image data of the patient generated by a first modality to form a registered system, determining, within the registered system, a location for placing an electrode on the patient based on an area of interest for the patient, and causing the robotic system to place the electrode at the location on the patient.

19 Claims, 3 Drawing Sheets

(56) References Cited

OTHER PUBLICATIONS

Cole et al. "Design of a Robotic System for MRI-Guided Deep Brain Stimulation Electrode Placement," 2009 IEEE International Conference on Robotics and Automation, May 17-19, 2009, Kobe, Japan, pp. 4450-4456.

Meng et al. "A stereotaxic image-guided surgical robotic system for depth electrode insertion," IEEE, 36th Annual International Conference of the IEEE Engineering in Medicine and Biology Society, Aug. 2014, pp. 6167-6170.

Tan et al. "Electrical Impedance Tomography for Robot-Aided Internal Radiation Therapy," Frontiers in Bioengineering and Biotechnology, Jun. 2021, vol. 9, Article 698068, 12 pages.

International Search Report and Written Opinion for International (PCT) Patent Application No. PCT/IL2022/051050, dated Jan. 24, 2023, 15 pages.

* cited by examiner

SYSTEMS, DEVICES, AND METHODS FOR ROBOTIC PLACEMENT OF ELECTRODES FOR ANATOMY IMAGING

FIELD

The present technology generally relates to systems, devices, and methods for robotic placement of electrodes for anatomy imaging or obtaining physiological electric signal (to be later analyzed and processed).

BACKGROUND

Surgical robots may assist a surgeon or other medical provider in carrying out a surgical procedure, or may complete one or more surgical procedures autonomously. Imaging or analysis of a physiological electric signal may be used by a medical provider for diagnostic and/or therapeutic purposes.

SUMMARY

Example aspects of the present disclosure include:

A method, comprising registering a robotic system with a patient based on first image data of the patient generated by a first modality to form a registered system; determining, within the registered system, a location for placing an electrode on the patient based on an area of interest for the patient; and causing the robotic system to place the electrode at the location on the patient.

Any of the aspects herein, further comprising: performing one or more scans of the patient to generate the first image data.

Any of the aspects herein, wherein the first modality corresponds to a modality that takes a body contour scan of the patient to generate the first image data.

Any of the aspects herein, further comprising: generating second image data with a second modality that uses the electrode on the patient and one or more other electrodes on the patient.

Any of the aspects herein, wherein the second modality corresponds to a modality that takes an electrical impedance tomography (EIT) scan of the patient to generate EIT data as the second image data.

Any of the aspects herein, further comprising: tracking a location of the electrode while generating the EIT data with the EIT scan; and adjusting the EIT data of the patient based on the tracked location.

Any of the aspects herein, wherein the location of the electrode is tracked based on output of a camera.

Any of the aspects herein, wherein the location of the electrode is tracked based on one or more signals associated with tracking the location of the electrode.

Any of the aspects herein, wherein the one or more signals associated with tracking the location of the electrode includes one or more received electrical signals or one or more induced electrical signals.

Any of the aspects herein, further comprising: registering an EIT image included in the EIT data with one or more other images of the patient generated by a third modality.

Any of the aspects herein, wherein the third modality corresponds to a modality that generates the one or more other images of the patient during a PET scan, an ultrasound scan, an X-ray scan, a CT scan, or an MRI scan.

Any of the aspects herein, further comprising: performing, using the electrode and one or more other electrodes on the patient, therapy on the patient.

A device, comprising: processing circuitry configured to: register a robotic system with a patient based on first image data of the patient generated by a first modality to form a registered system; determine, within the registered system, a location for placing an electrode on the patient based on an area of interest for the patient; and generate at least one first control signal that controls a robotic system to place the electrode at the location on the patient.

Any of the aspects herein, wherein the processing circuitry is configured to: generate at least one second control signal that is applied to the electrode or one or more other electrodes on the patient during a scan of the patient with a second modality that produces an electrical impedance tomography (EIT) image of the patient.

Any of the aspects herein, wherein the processing circuitry is configured to: track a location of the electrode during the scan that produces the EIT image of the patient; and adjust the EIT image of the patient based on the tracked location.

Any of the aspects herein, wherein the processing circuitry is configured to: register the EIT image with one or more other images of the patient generated by a third modality different from the second modality and the first modality.

A system, comprising: a robotic system including at least one robotic arm; and processing circuitry configured to: register the robotic system with a patient based on first image data of the patient generated by a first modality to form a registered system; determine, within the registered system, a location for placing an electrode on the patient based on an area of interest for the patient; generate at least one first control signal that controls the at least one robotic arm to place the electrode at the location on the patient; and generate at least one second control signal that is applied to the electrode or one or more other electrodes on the patient during a scan of the patient with a second modality.

Any of the aspects herein, wherein the second modality corresponds to a modality that produces an electrical impedance tomography (EIT) image of the patient.

Any of the aspects herein, wherein the first modality corresponds to a modality that produces a body contour image of the patient.

Any of the aspects herein, wherein the processing circuitry is configured to: register the EIT image with one or more other images of the patient generated by a third modality.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Electric Impedance Tomography (EIT) is an imaging technique that produces images based on the different electric impedances of different tissues within a patient's body. In general, EIT imaging is safer than other imaging techniques in that it that does not use ionizing radiation or potentially harmful ultrasound vibrations. Instead, EIT imaging is accomplished by placing electrodes on different parts of the patient's body. Once placed, some of the electrodes induce electrical signals into the patient's body while other ones of the electrodes sense the electrical signals that have passed through various anatomies within the patient's body. In at least one other embodiment, the electrodes only "read" the electric signal that is originated within the body, without inducing "synthetic" electric signal(s). EIT data gathered in this fashion may provide information beneficial for estimation of bone condition and the condition of soft and/or hard tissues. For example, a reconstruction algorithm may be applied to the EIT data to generate a 2D or 3D image of the electric impedance within the body, which in turn may enable a clinician to differentiate between the different tissues or glean additional information about the tissue condition.

In some EIT applications, individual electrodes or electrodes that are part of an electrode belt are placed on the patient's body manually by the clinician or a technician. Manual placement of the electrode belt or the individual electrodes on the patient may be a slow process and imprecise, which leads to inefficiencies and/or inaccuracies with the imaging process and resulting image data. In addition, during an EIT scan, the positions of the electrodes may change due to patient breathing or other patient movement, which may further reduce the quality of the image data gathered by the scan (e.g., reduce the quality of an EIT image with unintended artifacts).

Inventive concepts propose to address the above-described problems and other problems by controlling a robotic system with accurate knowledge of a patient's body to determine locations on the patient's body for the electrodes and to automatically place (e.g., without human intervention) the electrodes for an EIT scan on the patient to facilitate improved imaging results. In addition, automatic robotic electrode placement may be accomplished more quickly than manual placement. Still further, the electrodes may be monitored or tracked for movement that may negatively impact the imaging process. For example, during an EIT scan of a patient's heart, the electrodes may move due to patient breathing. Inventive concepts propose to monitor this movement in real time (e.g., with a camera and/or feedback from the electrodes themselves) to accurately track the locations of the electrodes during the scan. EIT data collected during the scan may then be adjusted to account for any electrode movement during image reconstruction, which may decrease image artifacts caused by the movement, thereby improving image quality of an EIT image reconstructed from the EIT data collected during the scan. Monitoring and/or tracking locations of electrodes may be accomplished with the electrodes themselves (e.g., based on signals induced by the electrodes to the patient and then sensed by other electrodes on the patient for the purpose of determining distance between the inducing and sensing electrodes) or by monitoring their movement through additional apparatus such as a camera. In any event, continuously monitoring real time locations of the electrodes may enable adjustment of measured EIT data to obtain real time images that are more accurately imaging the tissue characteristics.

In at least one embodiment, the robotic system may accurately and safely place the electrodes for EIT imaging and/or therapy inside a patient's body. Placing an electrode inside the patient's body during surgery or for the purpose of gathering EIT images to assist with performing surgery may offer a potential for gathering more information about the anatomy of the patient and further contribute to a safer clinical outcome. For example, EIT data and/or images may assist a clinician with differentiating between healthy and osteoporotic bone, healthy lungs vs. lungs with fluid, and/or other diagnoses.

Inventive concepts further propose to register an image captured with electrodes placed according to inventive concepts herein with an image from a different modality, such as an ultrasound scan, Mill scan, PET scan, X-ray scan, and/or CT scan. Registering, for example, an EIT image with another image from another modality may provide more reliable and comprehensive data that enables better decision making during and/or after a clinical procedure to achieve a fast and safe clinical outcome. For example, such image fusion may be carried out according to suitable registration algorithms on two images (e.g., an EIT image and an X-ray image) that were taken on a single co-registered system. In another example, EIT images may be registered with images from another modality taken prior to the EIT scan. Registering an EIT image with an image from another modality may be useful because images from ultrasound scan, MRI scans, X-ray scan, and the like generally have high spatial resolution that better enables anatomy\tissue discrimination. Registering EIT images with images from another modality may be useful for accurate placement of electrodes within the patient's body. In addition, co-registering EIT images with images from another modality may produce a fused image that provides more accurate clinical locations of high and low electric impedance areas of the patient's anatomy.

Inventive concepts further propose to extend robotic placement of electrodes to other applications that benefit from accurate electrode placement such as therapy that involves therapeutically treating a condition (e.g., pain) using electrical signals that pass through the same or similar electrodes used for EIT imaging purposes. Accurate robotic placement of the electrodes for therapy may improve the likelihood of a successful treatment while avoiding undesired tissue damage for healthy tissues surrounding the target tissue.

Embodiments of the present disclosure provide technical solutions to one or more problems associated with electrode placement for EIT imaging and/or electrode therapy. At least one embodiment additionally provides technical solutions to problems associated with generating accurate EIT images that may be registered with images from another modality to increase the amount of information a clinician can glean from the co-registered image. At least one embodiment additionally provides technical solutions to problems associated with movement of the electrodes during EIT imaging. These and other technical solutions should be apparent to one with skill in the art in view of the instant description.

Figure 1:
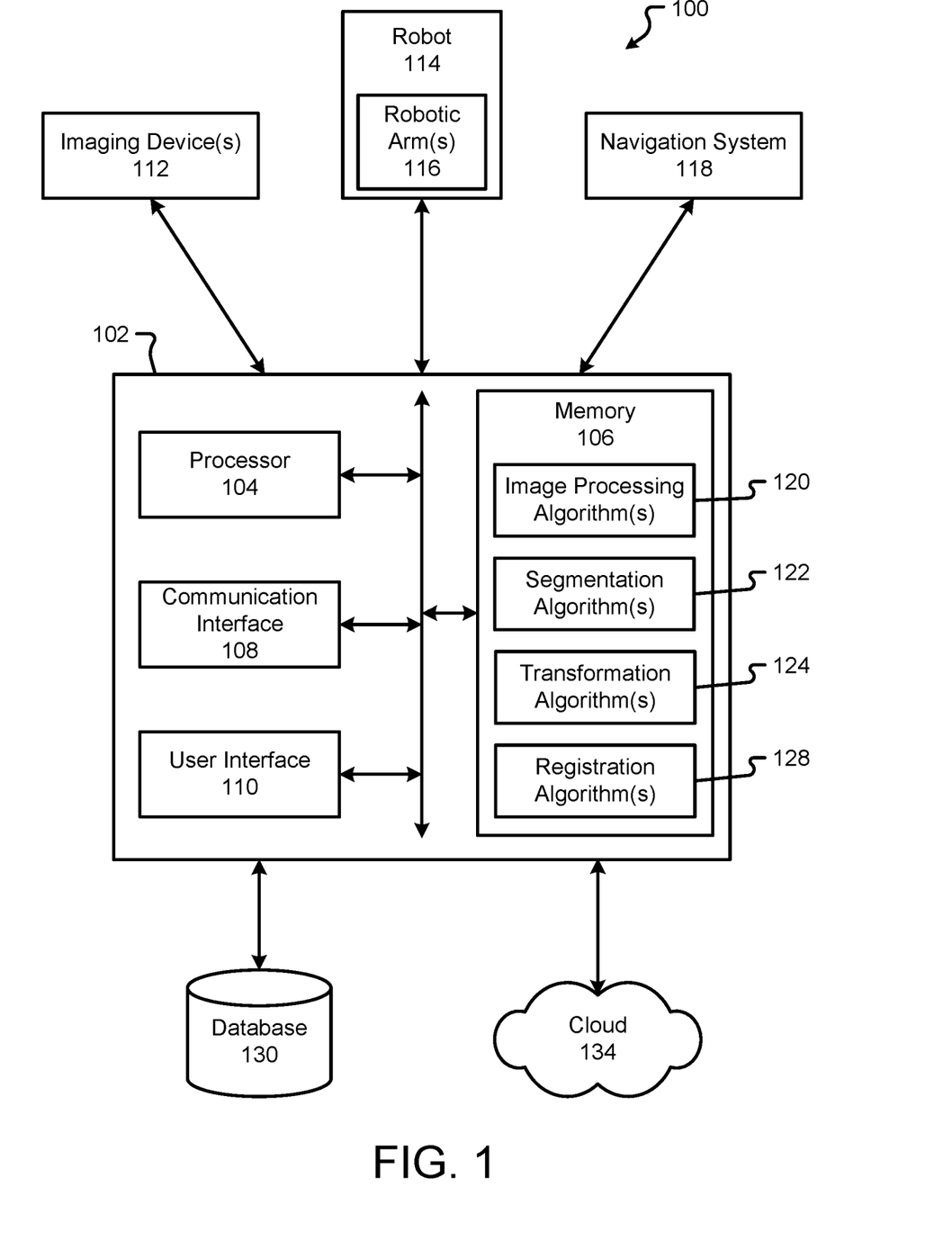
FIG. 1 is a block diagram of a system according to at least one embodiment of the present disclosure.

Turning first to FIG. 1, a block diagram of a system 100 according to at least one embodiment of the present disclosure is shown. The system 100 may be used to automatically place electrodes on a patient for the purpose of performing EIT imaging and/or electrode therapy and/or carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor or processing circuitry 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may comprise a microprocessor configured to execute instructions stored in the memory 106, which instructions may cause the processor 104 to carry out one or more computing steps utilizing or based on data received from the imaging device 112, the robot 114, the navigation system 118, the database 130, and/or the cloud 134. The processor 104 may comprise an ASIC, an FPGA, and/or suitable hardware and/or software for carrying out computing tasks for computing device 102.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200 and 300 described herein, or of any other methods. The memory 106 may store, for example, one or more image processing algorithms 120, one or more segmentation algorithms 122, one or more transformation algorithms 124, and/or one or more registration algorithms 128. One or more of the sets of algorithms stored in memory 106 may enable image registration between two or more images (e.g., an EIT image and an X-ray image) and/or coordinate system registration between two or more coordinate systems (e.g., a patient coordinate system and a robotic system coordinate system. Such instructions or algorithms may, in some embodiments, be organized into one or more applications, modules, packages, layers, or engines. Alternatively or additionally, the memory 106 may store other types of data (e.g., machine learning models, artificial neural networks, etc.) that can be processed by the processor 104 to carry out the various method and features described herein. Thus, although various components of memory 106 are described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transducer), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), an EIT system, and/or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (i.e., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system may comprise one or more electromagnetic sensors. In various embodiments, the navigation system 118 may be used to track a position and orientation (i.e., pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; one or more images useful for placing electrodes on and/or in a patient's body; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

Figure 2:
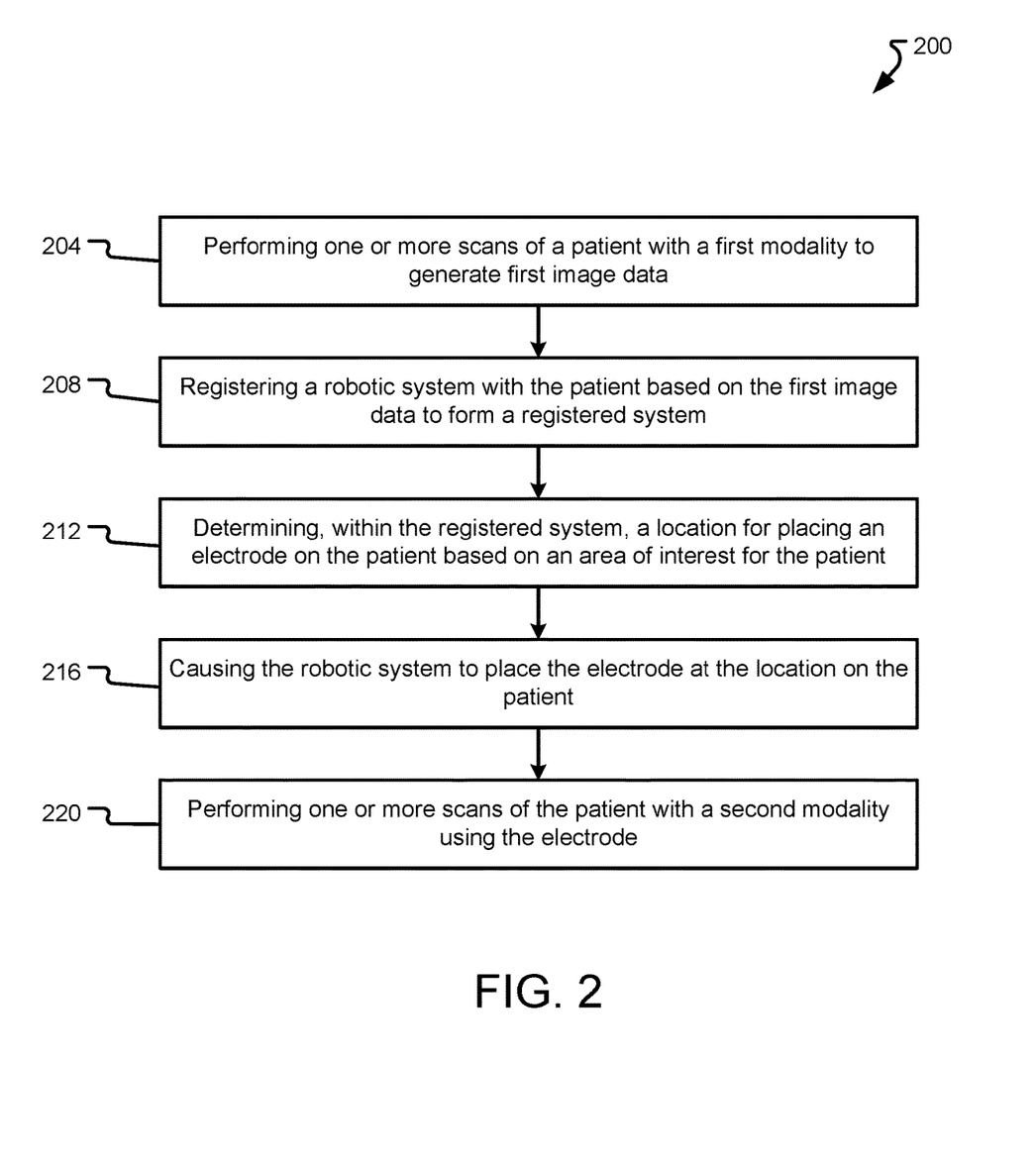
FIG. 2 is a flowchart according to at least one embodiment of the present disclosure.
Figure 3:
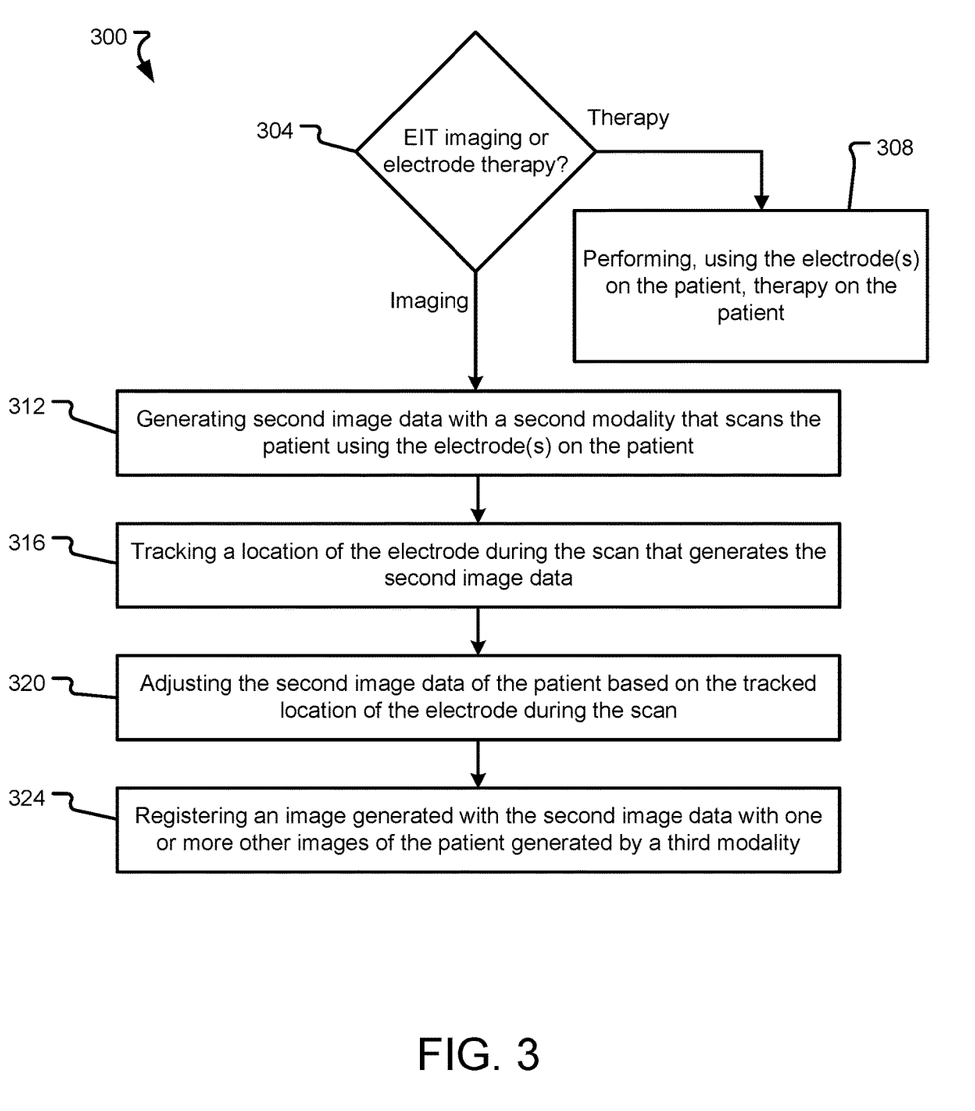
FIG. 3 is a flowchart according to at least one embodiment of the present disclosure.

The system 100 or similar systems may be used, for example, to carry out one or more aspects of any of the methods 200 and 300 described herein. The system 100 or similar systems may also be used for other purposes.

FIG. 2 depicts a method 200 that may be used, for example, to place electrodes on a patient's body according to at least one example embodiment.

The method 200 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 200. The at least one processor may perform the method 200 by executing instructions stored in a memory such as the memory 106. The instructions may correspond to one or more steps of the method 200 described below. The instructions may cause the processor to execute one or more algorithms, such as an image processing algorithm 120, a segmentation algorithm 122, a transformation algorithm 124, and/or a registration algorithm 128.

The method 200 comprises performing one or more scans of a patient to generate first image data (step 204). The one or more scans of the patient may be performed with an imaging device 112 of a first modality under control of the computing device 102. In at least one embodiment, the first modality corresponds to a modality that takes a body contour scan of the patient to generate the first image data. In this case, the first modality may correspond to a LIDAR camera system or depth camera that takes a full or partial body contour scan of the patient depending on body position of the patient that may be lying down, standing up, sitting, etc. However, example embodiments are not limited thereto, and the first modality may correspond to a modality that performs another type of scan such as a PET scan, an ultrasound scan, an X-ray scan, a CT scan, an MRI scan, and/or other suitable scan of the patient that may be considered useful for determining locations for placing electrodes on the patient. Step 204 may be omitted from the method 200 if, for example, the database 130 already contains the first image data from a previous scan of the patient with the first modality. In this case, the first image data from database 130 (or other source) is an input to step 208 described below.

The method 200 also comprises registering a robotic system with the patient based on the first image data of the patient generated by the first modality to form a registered system (step 208). The robotic system may include the robot 114 with robotic arms 116, one or more imaging devices 112, the navigation system 118, and/or a patient table on which a patient lies for undergoing surgery and/or imaging. For example, the computing device 104 may form the registered system by executing one or more suitable algorithms in memory 106 to correlate a coordinate system of the robot 114 with a coordinate system of a patient on a patient table using the body contour generated in step 204 so that the system 100 accurately tracks patient pose relative to poses of robotic arms 116 of the robot 114. As noted above, the patient table may be part of the robotic system, meaning that the robotic system already has accurate knowledge of the location of the patient table relative to other parts of the robotic system like robotic arms 116, and as such, the patient table does not necessarily need to be registered with the robotic system. However, the patient table may be additionally registered with the robotic system as part of step 208 if the patient table is not already in the same coordinate system as the robotic system.

In at least one embodiment, steps 204 and 208 occur in conjunction with one another so that the patient is already lying down on a patient table that is part of the robotic system when the body contour of the patient is generated in step 204, which enables step 208 to register the coordinate systems of the patient and the robotic system with one another based on the first image data generated in step 204 (where the first image data may correspond to a body contour of the patient).

The method 200 also comprises determining, within the registered system, a location for placing an electrode on the patient based on an area of interest for the patient (step 212). For example, a surgical or clinical plan for the patient may indicate that a certain part of the patient's anatomy is an area of interest. In at least one embodiment, the location for the electrode on the patient's body corresponds to a pose of the electrode on the patient's body. The area of interest may correspond to part of the patient's anatomy that is to be scanned upon placement of the electrode and/or one or more other electrodes. For example, the area of interest may correspond to the patient's heart, lungs, or other anatomical feature that requires scanning during surgery or for the purpose of performing a future surgery. In another example, the area of interest on the patient corresponds to a site for receiving electrode therapy upon placement of the electrode and/or one or more other electrodes. Here, the area of interest may correspond to the patient's torso, arms, legs, and/or other part of the body that is the intended target of therapy.

In at least one embodiment, the computing device 102 uses input from a neural network or machine learning algorithm trained with data from previous scans (EIT scans or otherwise) of the patient and/or of one or more other patients to determine the location of the electrode in step 212. For example, a neural network may use the body contour from step 204, the area of interest, the type of scan being performed, and a number of total electrodes to be placed as inputs to determine a pose of the electrode on the patient that results in an improved or optimal scan and/or therapeutic session. At least one embodiment involves an iterative process where the robotic system places one or more electrodes on the patient and then gathers information on signal quality from the electrodes, such as signal amplitude, signal to noise ratio (SNR), and/or the like. Electrodes that do not meet thresholds for signal quality may be repositioned by the robotic system until the thresholds are met or until signal quality is at least improved. Using this iterative method and/or using existing knowledge of the patient's anatomy, the robotic system may avoid placing electrodes on areas of the body that can interfere with induced and/or received electrical signals due to anatomical obstructions and/or implants already in the patient's body (e.g., metal implants). In at least one embodiment, electrode density is a factor taken into consideration when placing electrodes to avoid having too few or too many electrodes within a certain area of the patient's body.

The method 200 also comprises causing the robotic system to place the electrode at the location on the patient (step 216). In other words, step 216 includes controlling the robotic system within the registered system formed in step 208 to place the electrode at the location on the patient determined in step 212. For example, the computing device 102 controls a robotic arm 116 of the robot 114 to place the electrode at the location on the patient. In this case, the computing device 102 may generate at least one first control signal that controls the robot 114 of the robotic system to automatically place the electrode at the location on the patient. The at least one control signal may correspond to one or more electrical signals. The robot 114 may automatically place the electrode at the location on the patient in that little or no human intervention occurs during placement of the electrode by the robot 114.

Additionally or alternatively and as discussed in more detail below, the system may provide feedback that enables human intervention in the placement process or electrodes.

In at least one embodiment, a clinician or technician may be monitoring the electrode placement by the robotic system and receive real time feedback about where the robotic system has placed or is about to place a particular electrode. In this scenario, the feedback may be in the form of one or more images presented on the user interface 110 indicating where a current electrode is about to be placed on the body contour of the patient and/or where previous electrodes have been placed on the body contour of the patient. The person monitoring the feedback may provide input to the user interface 110 that accepts, rejects, and/or alters a proposed placement of an electrode or a previous placement of an electrode, thereby enabling human supervision of the automatic electrode placement by the robotic system. The system may be further capable of predicting effects of altering electrode placement and notifying the person monitoring the electrode placement of such effects. For example, the computing device 102 may utilize the above referenced neural network or machine learning algorithm trained with data from previous scans and/or treatments to predict the effects of placing electrodes at particular locations on the patient. The notifications of such effects may include general notifications such as "electrode placement may reduce (or improve) scan quality" or more include more specific notifications such as "electrode placement associated with heart scan."

At least one embodiment enables a clinician to place one or a few electrodes on the patient manually (with or without the assistance of robot 114) and then receive a notification from the system that provides one or more options for automatically placing remaining electrodes. For example, a clinician may intend to target the patient's lungs with a scan using electrodes and place one or two electrodes on the patient at or in proximity a location associated with scanning the patient's lungs. The system may detect, through one or more cameras, a location of the manually placed electrode(s) and render one or more options to the user interface 110 with suggestions for the area of interest based on the detected location(s) of the manually placed electrode(s). For example, upon detection that an electrode is manually placed on a patient's torso, the user interface 110 may display options for the clinician to select an area of interest as the patient's lungs, heart, or other anatomy within a torso that may be scanned. The clinician may select the appropriate area of interest to trigger automatic placement of remaining electrodes on the patient by the robotic system according to the selection.

It should be appreciated that steps 212 and 216 may be repeated for multiple electrodes if more than one electrode is desired to be automatically placed on the patient by the robotic system. For example, if the area of interest on the patient is the target for an EIT scan, then some or all of the electrodes used during the EIT scan may be placed on the patient according to steps 212 and 216. In this case, step 212 may include determining the locations for the electrodes as locations that are known to provide an improved or optimal EIT image of the area of interest after an EIT scan of the patient. In addition, it should be appreciated that although the method 200 has been described with reference to placing electrodes on a patient, the method 200 may also be useful for placing electrodes in a patient.

The method 200 also comprises performing one or more scans of the patient using the electrode (step 220). For example, the computing device 102 controls the system 100 to perform an EIT scan of the patient using the electrode or electrodes placed in step 216 in accordance with suitable EIT techniques, which may include using some of electrodes on the patient to induce electrical signals to the patient's body while using other electrodes on the patient to sense the induced electrical signals to generate EIT data. The computing device 102 may execute a suitable image processing algorithm 120 to generate one or more EIT images from the EIT data.

The present disclosure encompasses embodiments of the method 200 that comprise more or fewer steps than those described above, and/or one or more steps that are different than the steps described above.

FIG. 3 depicts a method 300 that may be used, for example, to carry out an imaging scan or therapy on a patient using the electrodes placed in the method 200.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing instructions stored in a memory such as the memory 106. The instructions may correspond to one or more steps of the method 300 described below. The instructions may cause the processor to execute one or more algorithms, such as an image processing algorithm 120, a segmentation algorithm 122, a transformation algorithm 124, and/or a registration algorithm 128.

The method 300 comprises determining whether the electrode(s) placed in the method 200 are for imaging (e.g., EIT imaging) or electrode therapy (step 304). Such a determination may be based on a clinical plan associated with the area of interest of the patient, where the plan may indicate whether the area of interest is a target of imaging or therapy. In some embodiments, the method 300 is substituted for step 220 in FIG. 2.

When the determination in step 304 is that the electrode(s) are for therapy, the method 300 comprises performing, using the electrode(s) on the patient, therapy on the patient (step 308). In this case, such therapy (also referred to as electrode therapy) may correspond to therapy that uses electrical signals provided by the electrode(s) to stimulate the area of interest on the patient to provide a therapeutic effect (e.g., pain relief or other achievable therapeutic effect).

When the determination in step 304 is that the electrode(s) are for imaging, the method 300 comprises generating second image data with a second modality that scans the patient using the electrode(s) on the patient (step 312). In accordance with at least one embodiment, the second modality corresponds to a modality that takes an EIT scan of the patient to generate EIT data as the second image data. Thus, the computing device 102 may generate at least one second control signal (e.g., one or more electrical signals) that is applied to the electrode(s) on the patient during the scan of the patient with the second modality that produces EIT data that is reconstructed into an EIT image of the area of interest of the patient. Step 312 may include the same or similar operations as step 220 in FIG. 2. However, example embodiments are not limited thereto, and any suitable modality that uses electrodes similar to or the same as electrodes used in an EIT scan may be employed to generate the second image data.

The method 300 also comprises tracking or monitoring a location of the electrode while generating the second image data (step 316). In at least one embodiment, the location(s) of the electrode(s) is(are) tracked based on output of a camera that tracks the electrode movement within the registered system using, for example, optical markers (e.g., reflectors or LEDs) or other suitable marker on each electrode that is identifiable by a camera. Additionally or alternatively, each electrode may include an RF transmitter that enables tracking using wireless signals that do not interfere with the induced and/or received electrical signals of the electrode.

In at least one other embodiment, the location of an electrode is tracked based on one or more signals from the electrode that are for tracking the electrode. The one or more signals associated with tracking the electrode may include one or more received electrical signals and/or one or more induced electrical signals having signal characteristics that are useful for determining locations of electrodes relative to one another. In this case, time-of-flight principles may be employed to determine a distance between an inducing electrode and a receiving electrode. For example, the time elapsed between inducing a signal to the patient with an inducing electrode and receiving a version of that signal by a receiving electrode may be used to determine a distance between the two electrodes. However, unlike traditional time-of-flight distance equations that assume light travels through free-space, example embodiments may employ modified distance equations that take into account the signal characteristics of the inducted electrical signal and the patient's anatomy as the medium through which the electrical signal travels. Such modified distance equations may be derived from simulations and/or trials. Here, it should be appreciated that the signals used for tracking electrodes may be different from signals used to scan the area of interest of the patient. In other words, some of the electrodes on the patient may be dedicated to inducing and/or sensing signals for the purpose of electrode location tracking while others of the electrodes on the patient may be dedicated to inducing and/or sensing signals for the purpose of generating image data as part of the scan (e.g., an EIT scan). In this case, locations of electrodes dedicated to generating image data may be interpolated from known locations of the electrodes being tracked.

Here, it should be appreciated that steps 312 and 316 may be performed concurrently so that the system gathers real time location information of the electrode(s) on the patient during the scan.

The method 300 also comprises adjusting the second image data from step 312 based on the tracked location(s) of the electrode(s) during the scan (step 320). In the scenario where the second image data corresponds to EIT data, step 320 includes adjusting the EIT data of the patient based on the tracked location(s) of electrode(s) on the patient. In at least one example, the second image data from step 312 and the tracked locations of electrodes from step 316 may be timestamped according to a same clock signal (or according to two clock signals with a known relationship). This enables the system to correlate the location of an electrode at a particular time with a subset of the second image data gathered at or near the electrode during the scan at the particular time. Thereafter, step 320 may adjust the subset of the second image data if, for example, the location of the electrode at the particular time is determined as a location has caused or may cause an artifact or other irregularity with the second image data. Adjusting the subset of the second image data may include modifying the subset of the second image data in a manner that reduces or removes the artifact or irregularity in a final set of second image data. For example, adjusting the subset of the second image data may include averaging the subset of the second image data with other subsets of the second image data determined to be taken at or near a same part of the area of interest as the subset of the second image data. In at least one embodiment, step 320 includes discarding the subset of the second image data and, in some cases, generating replacement image data according to a suitable interpolation algorithm that uses surrounding image data as reference points. Example embodiments are not limited to the above described methods of adjustment and other suitable adjustments of the second image data may be made.

The method 300 also comprises registering an image generated with the second image data with one or more other images of the patient generated by a third modality (step 324). For example, if the second image data corresponds to EIT data that is used to construct an EIT image, then the EIT image may be registered with one or more other images of the patient generated by the third modality according to a suitable algorithm in memory 106 (e.g., registration algorithm, image processing algorithm, and/or the like). The third modality may correspond to a modality that generates the one or more other images of the patient during a PET scan, an ultrasound scan, an X-ray scan, a CT scan, and/or an MRI scan. The third modality may be part of the registered system formed by the method 200 or the third modality may be registered in its own system separate from the registered system formed by the method 200.

As may be appreciated, step 324 results in a co-registered image that fuses, for example, an EIT image of the area of interest of the patient with another image of the area of interest of the patient (e.g., an X-ray image). A clinician or other interested party may then examine the co-registered image and draw one or more clinical conclusions about the area of interest of the patient based on the co-registered image. Because the co-registered image includes image information from two different modalities (e.g., an EIT scan and an X-ray scan), the co-registered may enable the clinician or other interested party to draw conclusions about the area of interest that are otherwise not possible or more difficult to see when looking at either image alone.

The present disclosure encompasses embodiments of the method 300 that comprise more or fewer steps than those described above, and/or one or more steps that are different than the steps described above.

As noted above, the present disclosure encompasses methods with fewer than all of the steps identified in FIGS. 2 and 3 (and the corresponding description of the methods 200 and 300), as well as methods that include additional steps beyond those identified in FIGS. 2 and 3 (and the corresponding description of the methods 200 and 300). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method, comprising:
   registering a robotic system with a patient based on first image data of the patient generated by a first modality to form a registered system, wherein the first image data corresponds to a depth image of a body contour of the patient;
   determining, by at least one processor and within the registered system and using the body contour of the patient, a location of an already placed electrode on the patient, the already placed electrode to be used for an electrical impedance tomography (EIT) scan of the patient;
   determining, by the at least one processor and based on the determined location of the already placed electrode, possible areas of interest on which to conduct the EIT scan;
   rendering, by the at least one processor, the possible areas of interest to a user interface;
   determining, by the at least one processor based on a selected area of interest from the possible areas of interest and using the depth image, one or more proposed locations on the patient for placing one or more additional electrodes;
   predicting an effect of using the one or more additional electrodes at the one or more proposed locations;
   generating a notification that informs a clinician of the predicted effect;
   receiving, based on input from the clinician, feedback that accepts the one or more proposed locations of the one or more additional electrodes; and
   generating, subsequent to receiving the feedback, at least one first control signal that controls a robotic arm of the robotic system to move within the registered system to place the one or more additional electrodes at the one or more proposed locations on the patient.

2. The method of claim 1, further comprising:
   performing one or more scans of the patient to generate the first image data.

3. The method of claim 1, wherein the first modality corresponds to a depth camera or a LIDAR system.

4. The method of claim 1, further comprising:
   performing the EIT scan of the patient using the already placed electrode and the one or more additional electrodes on the patient to generate EIT data.

5. The method of claim 4, further comprising:
   tracking a current location of the already placed electrode and current locations of the one or more additional electrodes while generating the EIT data of the patient with the EIT scan; and
   adjusting the EIT data of the patient based on the tracking.

6. The method of claim 5, wherein the current locations of the already placed electrode and the one or more additional electrodes are tracked based on output of a camera.

7. The method of claim 5, wherein the current locations of the already placed electrode and the one or more additional electrodes are tracked based on one or more electrical signals.

8. The method of claim 7, wherein the one or more electrical signals include one or more received electrical signals or one or more induced electrical signals.

9. The method of claim 4, further comprising:
   registering an EIT image included in the EIT data with one or more other images of the patient generated by a third modality.

10. The method of claim 9, wherein the third modality corresponds to a modality that generates the one or more other images of the patient during a PET scan, an ultrasound scan, an X-ray scan, a CT scan, or an MRI scan.

11. The method of claim 1, further comprising:
    performing, using the already placed electrode and the one or more additional electrodes on the patient, therapy on the patient.

12. A device, comprising:
    processing circuitry configured to:
    register a robotic system with a patient based on first image data of the patient generated by a first modality to form a registered system, wherein the first image data corresponds to a depth image of a body contour of the patient;
    determine, within the registered system and using the body contour of the patient, a location of an already placed electrode on the patient, the already placed electrode to be used for an electrical impedance tomography (EIT) scan of the patient;
    determine, based on the determined location of the already placed electrode, possible areas of interest on which to conduct the EIT scan;

render the possible areas of interest to a user interface;
determine, based on a selected area of interest from the possible areas of interest and using the depth image, one or more proposed locations on the patient for placing one or more additional electrodes;
predict an effect of using the one or more additional electrodes at the one or more proposed locations;
generate a notification that informs a clinician of the predicted effect;
receive, based on input from the clinician, feedback that accepts the one or more proposed locations of the one or more additional electrodes; and
generate, subsequent to receiving the feedback, at least one first control signal that controls a robotic arm of the robotic system to move within the registered system to place the one or more additional electrodes at the one or more proposed locations on the patient.

13. The device of claim 12, wherein the processing circuitry is configured to:
generate at least one second control signal that is applied to the already placed electrode and the one or more additional electrodes during the EIT scan of the selected area of interest of the patient to produce an (EIT) image.

14. The device of claim 13, wherein the processing circuitry is configured to:
track current locations of the already placed electrode and the one or more additional electrodes during the scan that produces the EIT image of the patient; and
adjust the EIT image of the patient based on the tracked current locations.

15. The device of claim 13, wherein the processing circuitry is configured to:
register the EIT image with one or more other images of the patient generated by a second modality different from the first modality.

16. A system, comprising:
a robotic system including at least one robotic arm; and
processing circuitry configured to:
register the robotic system with a patient based on first image data of the patient generated by a first modality to form a registered system, wherein the first image data corresponds to a depth image of a body contour of the patient;
determine, within the registered system and using the body contour of the patient, a location of an already placed electrode on the patient, the already placed electrode to be used for an electrical impedance tomography (EIT) scan of the patient;
determine, based on the determined location of the already placed electrode, possible areas of interest on which to conduct the EIT scan;
render the possible areas of interest to a user interface;
determine, based on a selected area of interest from the possible areas of interest and using the depth image, one or more proposed locations on the patient for placing one or more additional electrodes;
predict an effect of using the one or more additional electrodes at the one or more proposed locations;
generate a notification that informs a clinician of the predicted effect;
receive, based on input from the clinician, feedback that accepts the one or more proposed locations of the one or more additional electrodes; and
generate, subsequent to receiving the feedback, at least one first control signal that controls the at least one robotic arm to move within the registered system to place the one or more additional electrodes at the one or more proposed locations on the patient.

17. The system of claim 16, wherein the processing circuitry is configured to:
generate at least one second control signal that is applied to the already placed electrode or the one or more additional electrodes on the patient during the EIT scan of the patient.

18. The system of claim 16, wherein the first modality corresponds to a depth camera or a LIDAR system.

19. The system of claim 17, wherein the processing circuitry is configured to:
register an EIT image from the EIT scan with one or more other images of the patient generated by a second modality.

* * * * *